United States Patent
Machida et al.

(10) Patent No.: US 9,849,170 B2
(45) Date of Patent: Dec. 26, 2017

(54) MICRONEEDLE COATING COMPOSITION AND MICRONEEDLE DEVICE

(71) Applicants: HISAMITSU PHARMACEUTICAL CO., INC., Tosu-shi, Saga (JP); THE CHEMO-SERO-THERAPEUTIC RESEARCH INSTITUTE, Kumamoto-shi, Kumamoto (JP)

(72) Inventors: Kazuya Machida, Tsukuba (JP); Seiji Tokumoto, Tsukuba (JP); Kazuyoshi Kaminaka, Kikuchi (JP); Yuji Ishikawa, Kumamoto (JP)

(73) Assignees: HISAMITSU PHARMACEUTICAL CO., INC., Tosu-Shi, Saga (JP); THE CHEMO-SERO-THERAPEUTIC RESEARCH INSTITUTE, Kumamoto-Shi, Kumamoto (JP)

( * ) Notice: Subject to any disclaimer, the term of this patent is extended or adjusted under 35 U.S.C. 154(b) by 0 days.

(21) Appl. No.: 14/766,922

(22) PCT Filed: Feb. 12, 2014

(86) PCT No.: PCT/JP2014/053198
§ 371 (c)(1),
(2) Date: Aug. 10, 2015

(87) PCT Pub. No.: WO2014/126105
PCT Pub. Date: Aug. 21, 2014

(65) Prior Publication Data
US 2016/0000898 A1    Jan. 7, 2016

(30) Foreign Application Priority Data
Feb. 13, 2013 (JP) ................................ 2013-025955

(51) Int. Cl.
*A61K 38/00* (2006.01)
*A61K 39/12* (2006.01)
(Continued)

(52) U.S. Cl.
CPC ............ *A61K 39/12* (2013.01); *A61K 9/0021* (2013.01); *A61K 47/12* (2013.01); *A61K 47/183* (2013.01);
(Continued)

(58) Field of Classification Search
CPC ........ A61K 38/00; A61K 47/02; A61K 47/12; A61K 47/183; A61K 9/0021;
(Continued)

(56) References Cited

U.S. PATENT DOCUMENTS

| | | | |
|---|---|---|---|
| 2005/0106209 A1 | 5/2005 | Ameri et al. | |
| 2008/0213461 A1 | 9/2008 | Gill et al. | |
| 2014/0330198 A1* | 11/2014 | Zhang | A61K 9/0021 604/46 |

FOREIGN PATENT DOCUMENTS

| | | |
|---|---|---|
| CN | 1901841 A | 1/2007 |
| CN | 102917722 A | 2/2013 |

(Continued)

OTHER PUBLICATIONS

Editing Tip: Parenthetical Elements [online] retrieved on Jun. 9, 2016 from: http://www.aje.com/en/arc/editing-tip-parenthetical-elements/; 5 pages.*

(Continued)

*Primary Examiner* — Ernst V Arnold
(74) *Attorney, Agent, or Firm* — Nath, Goldberg & Meyer; Joshua B. Goldberg; Tanya E. Harkins

(57) ABSTRACT

Disclosed is a microneedle coating composition comprising a Japanese encephalitis vaccine antigen, a basic amino acid, and an acid, wherein the mole number of the acid for one (Continued)

mole of the basic amino acid is larger than 1/(N+1) and less than 2, where N represents the valence of the acid.

10 Claims, 4 Drawing Sheets

(51) Int. Cl.
  *A61K 47/12* (2006.01)
  *A61K 9/00* (2006.01)
  *A61K 47/18* (2017.01)
  *C12N 7/00* (2006.01)
  *A61K 39/00* (2006.01)

(52) U.S. Cl.
  CPC ............ *C12N 7/00* (2013.01); *A61K 2039/54* (2013.01); *C12N 2770/24134* (2013.01)

(58) Field of Classification Search
  CPC .............. A61L 2300/214; A61L 31/16; A61M 37/0015; A61M 5/329
  See application file for complete search history.

(56) References Cited

FOREIGN PATENT DOCUMENTS

| JP | 2007511508 A | 5/2007 |
|---|---|---|
| JP | 2007527392 A | 9/2007 |
| JP | 2007536988 A | 12/2007 |
| JP | 2008528509 A | 7/2008 |
| WO | 2010/013601 A1 | 2/2010 |
| WO | 2011/150144 A2 | 12/2011 |

OTHER PUBLICATIONS

Ejima et al. (BioProcess International. 2005 pp. 20-22, 24, 26 and 28).*
International Patent Application No. PCT/JP2014/053198, International Search report dated Mar. 11, 2014. two (2) pages.
International Patent Application No. PCT/JP2014/053198, International Preliminary Report on Patentability dated Aug. 18, 2015, six (6) pages.
Search Report dated Aug. 16, 2016, for counterpart European Patent Application No. 14751836.9.
Schneider, Curtiss P."Arginine and the Hofmeister Series: The Role of Ion-Ion Interactions in Protein Aggregation Suppression"; Journal of Physical Chemistry Part B; Condensed Matter, Materials, Surfaces, Interfaces & Biophysical; vol. 115; No. 22; ISSN:1520-6106; DOI:10-1021/jp11120y; Jun. 9, 2011; p. 7447-7458; XP55300267.
European Search Report dated Sep. 15, 2016 corresponding to application No. 14751401.2-1455.
Office Action dated Dec. 1, 2016 corresponding to Taiwanese application No. 103104725.

* cited by examiner

US 9,849,170 B2

MICRONEEDLE COATING COMPOSITION AND MICRONEEDLE DEVICE

This is a National Phase Application filed under 35 U.S.C. 371 as a national stage of PCT/JP2014/053198, filed Feb. 12, 2014, an application claiming the benefit of Japanese Application No. P2013-025955, filed Feb. 13, 2013, the content of each of which is hereby incorporated by reference in its entirety.

TECHNICAL FIELD

The present invention relates to a microneedle coating composition and a microneedle device.

BACKGROUND ART

As a means for percutaneously administering an agent, a microneedle device is known. In some of such devices, a coating containing a drug and a thickener is formed (for example, Patent Literature 1).

In addition, a composition including a preparation composed of a biologically active substance and a viscosity-enhancing counterion (Patent Literature 2) and a coating formulation having a pH less than about 6 and containing at least one low-volatile counterion (Patent Literature 3) are known. Furthermore, a composition including a preparation composed of a therapeutically effective amount of a peptide agent and at least one counterion (Patent Literature 4) and a composition including a preparation composed of a biologically active ingredient and non-volatile counterion, having enhanced pH stability and solubility when dried (Patent Literature 5) are known. There is, in addition to these compositions, a coating containing a biological active substance and an additive, where a low content of an amino acid is used as an example of the additive (Patent Literature 6).

CITATION LIST

Patent Literature

Patent Literature 1: US 2008/0213461 A1
Patent Literature 2: JP-T-2007-511508
Patent Literature 3: JP-T-2007-536988
Patent Literature 4: JP-T-2008-528509
Patent Literature 5: JP-T-2007-527392
Patent Literature 6: WO 2011/150144

SUMMARY OF INVENTION

Technical Problem

However, it has been found that in Patent Literatures 1 and 2, the stability of physiologically active substances, such as protein, contained in agents is insufficient when the compositions contain materials exemplified as thickeners.

Accordingly, it is an object of the present invention to provide a microneedle coating composition capable of stabilizing the Japanese encephalitis vaccine antigen contained therein and a microneedle device including a coating layer formed from the composition.

Solution to Problem

The microneedle coating composition of the present invention comprises a Japanese encephalitis vaccine antigen, a basic amino acid, and an acid, wherein the mole number of the acid for one mole of the basic amino acid is larger than $1/(N+1)$ and less than 2, where N represents the valence of the acid.

When the mole number of the acid for one mole of the basic amino acid is $1/(N+1)$ or less, since the content of the acid in the coating composition is low, the coating composition cannot dissolve the basic amino acid. In contrast, when the mole number of the acid for one mole of the basic amino acid is 2 or more, since the content of the basic amino acid in the coating composition is low, the stability of the Japanese encephalitis vaccine antigen is reduced. Accordingly, the coating composition allows the Japanese encephalitis vaccine antigen contained therein to be stably present, by adjusting the numbers of moles of the acid for one mole of the basic amino acid within the above-mentioned range.

In the microneedle coating composition, the acid is preferably an acid having a melting point of 40° C. or more, more preferably at least one acid selected from the group consisting of phosphoric acid, lactic acid, benzoic acid, maleic acid, citric acid, tartaric acid, succinic acid, ascorbic acid, and aspartic acid, and most preferably at least one acid selected from the group consisting of phosphoric acid, citric acid, and tartaric acid. The use of such an acid can increase the concentration of the basic amino acid in the coating composition and can further improve the stability of the Japanese encephalitis vaccine antigen contained in the coating composition.

In the microneedle coating composition, the basic amino acid is preferably arginine The use of arginine as the basic amino acid can notably improve the stability of the Japanese encephalitis vaccine antigen in the coating composition.

The microneedle coating composition preferably comprises lysine or lysine hydrochloride. The addition of lysine or lysine hydrochloride can further improve the stability of the Japanese encephalitis vaccine antigen.

The present invention also provides a microneedle device including a coating layer formed from the microneedle coating composition on a microneedle. Here, the coating layer is preferably formed on the tip portion of the microneedle and more preferably formed only on the tip portion of the microneedle.

Advantageous Effects of Invention

According to the present invention, it is possible to provide a microneedle coating composition that can stabilize the Japanese encephalitis vaccine antigen contained therein and a microneedle device.

DESCRIPTION OF EMBODIMENTS

Preferred embodiments will now be described with reference to the drawings. Note that in the description of the drawings, the same elements are denoted by the same reference symbols, and the repeated description will be omitted. A part of the drawings is exaggeratedly drawn for easy understanding, and the dimensional ratios do not necessarily agree with those in the description.

Figure 1:
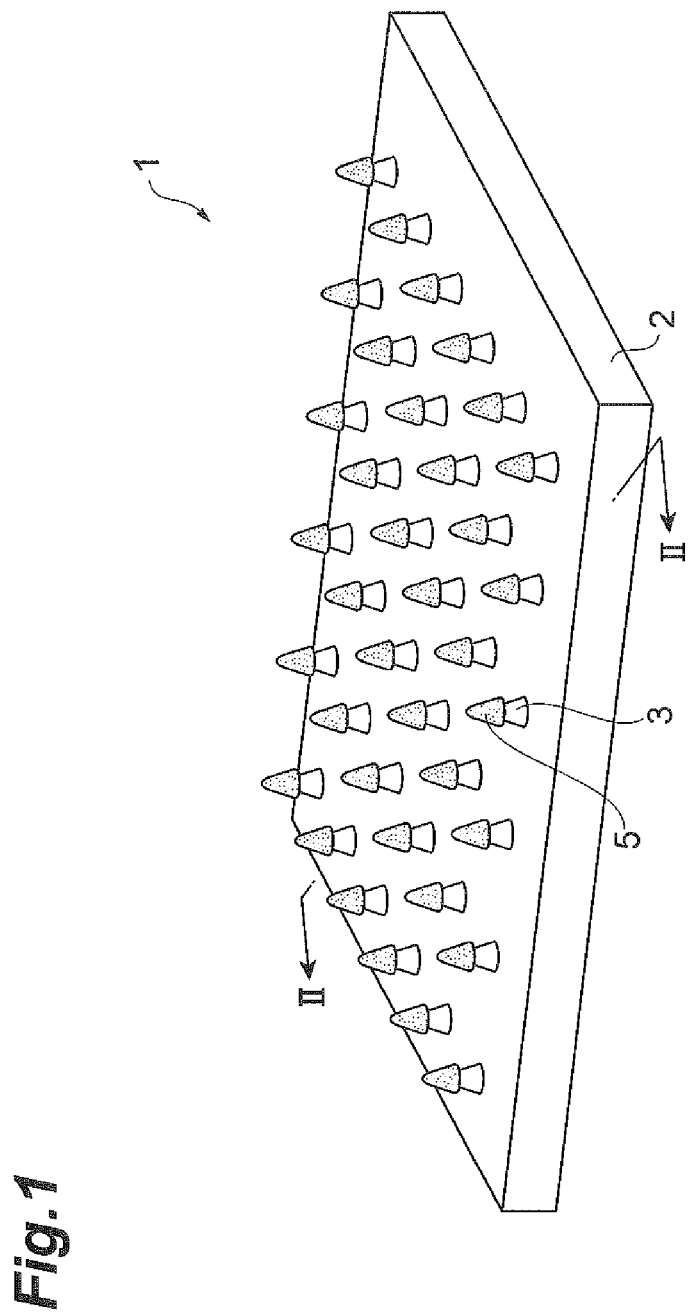
FIG. 1 is a perspective view illustrating an embodiment of a microneedle device.

FIG. 1 is a perspective view illustrating an embodiment of a microneedle device. The microneedle device 1 shown in FIG. 1 includes a substrate 2, a plurality of microneedles 3 two-dimensionally arranged on the substrate 2, and coating layers 5 disposed on the microneedles 3. The coating layers 5 are formed from the microneedle coating composition of the present invention, and it is preferable to remove at least part of the volatile component.

The substrate 2 is a base for supporting the microneedles 3. The area of the substrate 2 is preferably 0.5 to 10 cm$^2$, more preferably 1 to 5 cm$^2$, and further preferably 1 to 3 cm$^2$. A substrate having a desired size may be constituted by binding a plurality of the substrates 2.

The microneedles 3 each have a microstructure preferably having a height (length) of 50 to 600 μm. Here, the administration of the Japanese encephalitis vaccine antigen contained in the microneedle coating composition is ensured by adjusting the length of the microneedles 3 to 50 μm or more. In addition, by adjusting the length of the microneedles 3 to 600 μm or less, it is possible to prevent the microneedles from coming into contact with the nerves and thereby certainly reduce a risk of pain and to certainly prevent a risk of bleeding. In addition, when the lengths of the microneedles 3 are 500 μm or less, the Japanese encephalitis vaccine antigen can be efficiently administered in an amount that should enter within the skin, and administration without perforating the basal membrane is possible. The lengths of the microneedles 3 are particularly preferably 300 to 500 μm.

Here, the microneedles 3 are each a convex structure and mean a structure in an acicular shape or including an acicular shape in a broad sense. The microneedle is not limited to acicular one having a sharp tip and may be one having a blunt tip. When the microneedle 3 has a conical structure, the diameter at the base is preferably about 50 to 200 μm. Although the microneedles 3 are conical in this embodiment, the shapes of the microneedles may be a polygonal pyramid, such as quadrangular pyramid, or another shape.

The microneedles 3 are typically disposed with spaces therebetween to give a density such that about one to ten microneedles are disposed for 1 millimeter (mm) of the row of the needles. In general, adjacent rows are apart from each other by a distance substantially the same as the space between the needles in a row, and the density of needles is 100 to 10000 needles per 1 $cm^2$. A density of 100 needles or more can efficiently perforate the skin. In contrast, a density exceeding 10000 needles is difficult to maintain the strength of the microneedles 3. The density of the microneedles 3 is preferably 200 to 5000 needles, more preferably 300 to 2000 needles, and further preferably 400 to 850 needles.

Examples of the material of the substrate 2 or the microneedles 3 include silicon, silicon dioxide, ceramic, metals (such as stainless steel, titanium, nickel, molybdenum, chromium, and cobalt), and synthetic or natural resin materials, and considering the antigenicity of the microneedle and the unit price of the material, the material is particularly preferably a biodegradable polymer, such as polylactic acid, polyglycolide, polylactic acid-co-polyglycolide, pullulan, capronolactone, polyurethane, or polyanhydrate, or a non-biodegradable polymer, for example, a synthetic or natural resin material, such as polycarbonate, polymethacrylic acid, ethylene vinyl acetate, polytetrafluoroethylene, or polyoxymethylene. In addition, polysaccharides, such as hyaluronic acid, sodium hyaluronate, pullulan, dextran, dextrin, and chondroitin sulfate, are also preferred.

Examples of the method of producing the substrate 2 or the microneedles 3 include a wet etching process and dry etching process using silicon substrates, precision machining using a metal or resin (such as electric discharge processing, laser processing, dicing processing, hot emboss processing, and injection molding processing), and mechanical cutting. The substrate 2 and microneedles 3 are integrally molded by these processing methods. Examples of a method for making the microneedles 3 hollow include a method involving making microneedles 3 and then subjecting the microneedles 3 to secondary processing with laser for example.

The microneedle device 1 includes a coating layers 5 on the microneedles 3, and it is preferable to form the coating layers 5 by application of a microneedle coating composition. Examples of the method of application include spray coating and dip coating, and the dip coating is preferred. In FIG. 1, although the coating layers 5 are formed on all the microneedles 3, the coating layers 5 may be formed only on a part of the plurality of microneedles 3. In addition, in FIG. 1, the coating layers 5 are formed only on the tip portions of the microneedles 3 but may be formed so as to cover the entire of each of the microneedles 3. Furthermore, the coating layers 5 may be formed on the substrate 2.

FIGS. 3(*a*), (*b*), and (*c*) are diagrams illustrating an embodiment of the method of producing a microneedle device 1. In this method, first, as shown in FIG. 3(*a*), the microneedle coating composition 10 is swept on a mask plate 11 with a spatula 12 in the direction of the arrow A. By doing so, opening portions 13 are filled with the microneedle coating composition 10. Subsequently, as shown in FIG. 3(*b*), microneedles 3 are inserted into the opening portions 13 of the mask plate 11. Subsequently, as shown in FIG. 3(*c*), the microneedles 3 are pulled out from the opening portions 13 of the mask plate 11. By doing so, the microneedle coating composition 10 is allowed to adhere onto the microneedles 3. The microneedle coating composition 10 may adhere onto the substrate 2. Subsequently, the volatile component in the microneedle coating composition 10 on the microneedles 3 is removed by a known method, i.e., air drying, vacuum drying, or combination thereof. By doing so, the coating layers 5 rigidly adhere onto the microneedles 3 and typically become into a glassy or solid shape to produce a microneedle device. The moisture content of the coating layers 5 is usually 55% by mass or less, preferably 30% by mass or less, and further preferably 10% by mass or less, based on the total mass of the coating layers 5. The above-described method prevents the adhering microneedle coating composition 10 from dripping. The term dripping refers to flowing of the coating composition from the needle tip and means that the H portion in FIG. 3(*c*) gets longer.

The heights H of the coating layers 5 adhering to the microneedles 3 are adjusted by the clearance (gap) C shown in FIG. 3(*b*). This clearance C is defined by the distance from the bases of the microneedles 3 to the surface of the mask plate 11 (the thickness of the substrate 2 is not involved in the clearance C), and is determined depending on the tension of the mask plate 11 and the lengths of the microneedles 3. The range of the distance of the clearance C is preferably 0 to 500 μm. When the distance of the clearance C is zero, it means that the microneedle coating composition 10 is applied to the entire of each of the microneedle 3. The height H of the microneedle coating composition 10 adhering onto each of the microneedles 3 varies depending on the height of the microneedle 3 and can be 0 to 500 µm, usually 10 to 500 µm, preferably about 30 to 300 µm, and particularly preferably about 40 to 250 µm. In order to effectively use the Japanese encephalitis vaccine antigen in the microneedle coating composition 10, it is preferable to localize the microneedle coating composition 10 at a part of each of the microneedles, i.e., the tip portion of the needle, and also from the viewpoint of stimulation of the skin and the transfer ratio of a drug to the skin, it is preferable to localize the composition 10 in the area of 200 µm from the tip. Furthermore, from the viewpoint of stability of the Japanese encephalitis antigen vaccine, when the concentration of the Japanese encephalitis vaccine antigen is 0.1 to 10% w/w based on the total mass of the coating layer 5, it is more preferable to localize the microneedle coating composition 10 in the area of 50 to 150 µm from the tip. Since the microneedle coating composition 10 allows a basic amino acid to be dissolved in an aqueous solution at a high concentration (for example, 20% w/w or more) and has a high viscosity, it is possible to form the coating layers 5 on a part of each of the microneedles. The microneedle coating composition 10 held on the microneedles 3 in such a form is inserted into the skin simultaneously when the microneedles 3 are punctured into the skin.

The thickness of each of the coating layers 5 adhering on the microneedles 3 after drying is preferably less than 50 µm, more preferably less than 40 µm, and further preferably 1 to 30 µm. In general, the thickness of the coating layer 5 adhering to the microneedle is the average of the thicknesses measured over the surface of the microneedle 3 after drying. The thickness of each of the coating layers 5 adhering on the surface of the microneedles 3 can be increased by applying a plurality of coating films of the microneedle coating composition 10, that is, by repeating the adhering step after adhesion of the microneedle coating composition 10.

In adhesion of the microneedle coating composition 10 to the microneedles 3, it is preferable to maintain the temperature and humidity of the installation environment of the apparatus constant. In addition, when the microneedle coating composition 10 comprises water, the environment can be filled with water, as needed. By doing so, transpiration of the water in the microneedle coating composition 10 can be prevented as much as possible.

Figure 2:
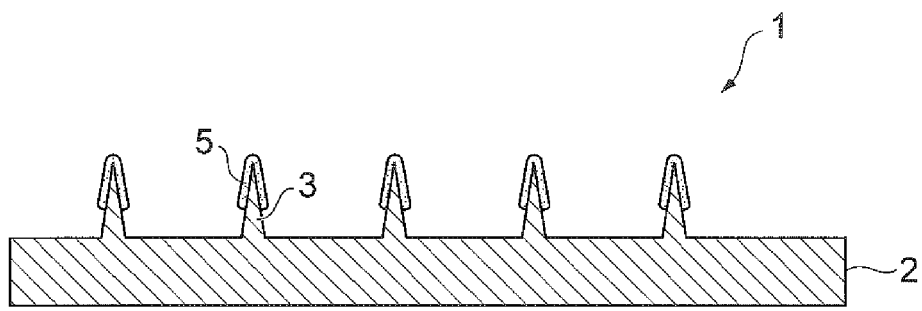
FIG. 2 is a cross-sectional view taken along the line II-II of FIG. 1.
Figure 3:
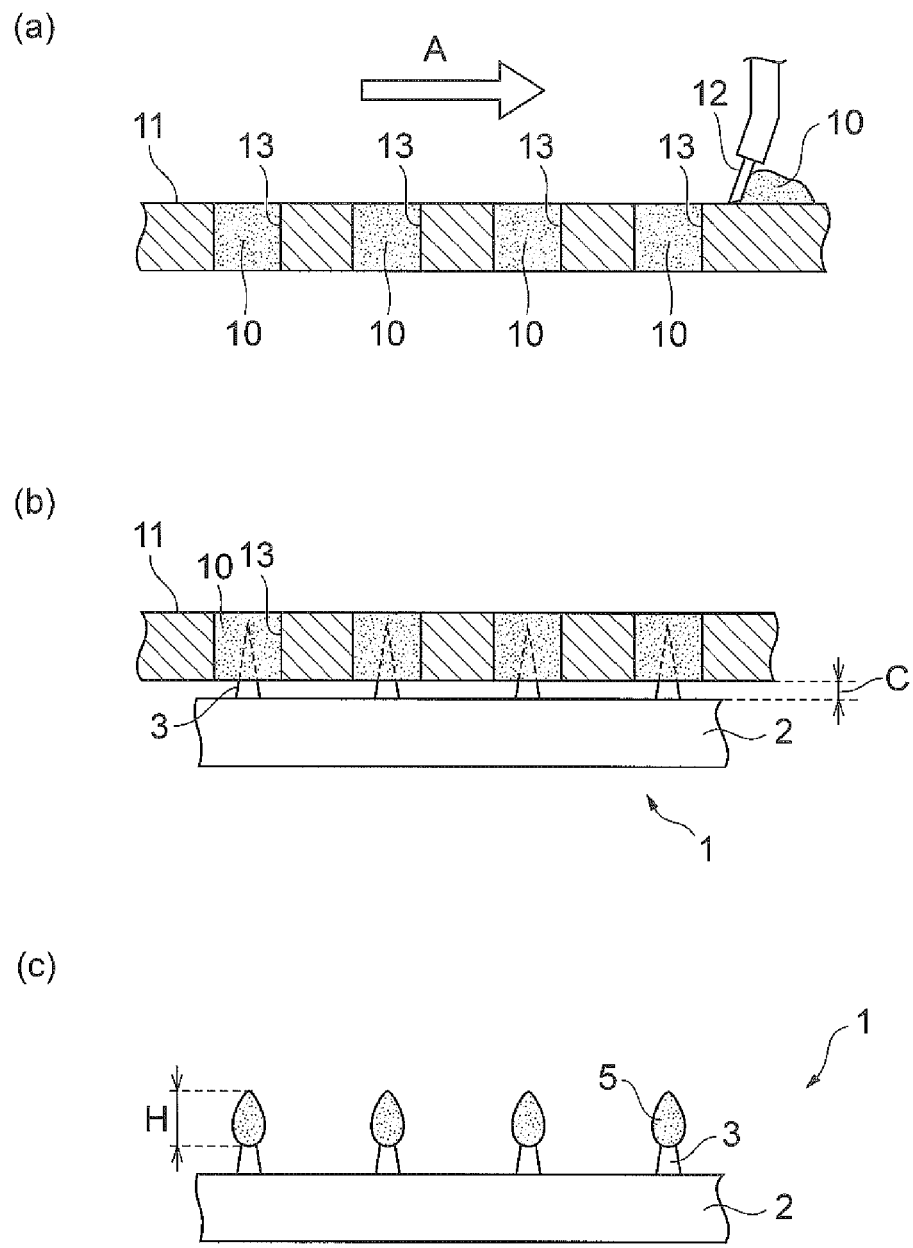
FIG. 3 includes diagrams (a), (b), and (c) illustrating an embodiment of a method of producing a microneedle device.

FIG. 2 is a cross-sectional view taken along the line II-II of FIG. 1. As shown in FIG. 2, the microneedle device 1 includes a substrate 2, microneedles 3 disposed on the substrate 2, and coating layers 5 disposed on the microneedles 3. The coating layers 5 adhering to the microneedles comprise a Japanese encephalitis vaccine antigen, a basic amino acid, and an acid and can be produced, for example, through the above-described process.

The microneedle coating composition 10 comprises a Japanese encephalitis vaccine antigen, a basic amino acid, and an acid, wherein the mole number of the acid for one mole of the basic amino acid is larger than 1/(N+1) and less than 2, where N represents the valence of the acid. The mole number of the acid for one mole of the basic amino acid is preferably 1/N or more and 1 or less.

The concentration of the Japanese encephalitis vaccine antigen in the microneedle coating composition 10 is preferably 0.01 to 30% w/w, more preferably 0.02 to 20% w/w, and further preferably 0.05 to 10% w/w, based on the total mass of the microneedle coating composition 10. If the concentration of the Japanese encephalitis vaccine antigen is 0.01% w/w or more, in the administration to the skin, an effective amount of the Japanese encephalitis vaccine antigen can be released inside the skin to exhibit a sufficient drug efficacy. The concentration of the Japanese encephalitis vaccine antigen in each of the coating layers 5 prepared by applying the microneedle coating composition 10 to the microneedles 3 and removing the volatile component is preferably 0.01 to 30% w/w, more preferably 0.03 to 15% w/w, and further preferably 0.1 to 10% w/w, based on the total mass of the coating layer 5.

The basic amino acid is not particularly limited and is one or more of, for example, lysine, histidine, arginine, ornithine, and carnitine and is preferably a free form thereof. In particular, arginine is preferred from the point of broadening the selection range of the acid.

The concentration of the basic amino acid in the microneedle coating composition 10 is preferably 20% w/w or more, and more preferably 30% w/w or more, based on the total mass of the microneedle coating composition 10, from the viewpoint of the viscosity and the stability of the Japanese encephalitis vaccine antigen. A concentration of the basic amino acid of 20% w/w or more can improve the stability of the Japanese encephalitis vaccine antigen in the microneedle coating composition 10. A concentration of the basic amino acid of 70% w/w or less makes the handling in the application to the microneedles 3 easy. In addition, the concentration of the basic amino acid in the coating layers 5 prepared by applying the microneedle coating composition 10 to the microneedles 3 and removing the volatile component is preferably 50 to 90% w/w and more preferably 60 to 80% w/w based on the total mass of the coating layer 5.

The ratio of the blending quantity (mass) of the basic amino acid to the blending quantity (mass) of the Japanese encephalitis vaccine antigen in the microneedle coating composition 10 is preferably 1.8 to 2400, more preferably 3.5 to 700, and further preferably 5 to 500. The stability of the Japanese encephalitis vaccine antigen can be improved by adjusting the ratio of the concentration of the basic amino acid to the concentration of the Japanese encephalitis vaccine antigen within the above-mentioned range.

The acid in the microneedle coating composition 10 is preferably an acid having a melting point of 40° C. or more. The use of such an acid allows the basic amino acid to be present at a high concentration (for example, 20% w/w or more) in the microneedle coating composition 10 and can improve the stability of the Japanese encephalitis vaccine antigen in the microneedle coating composition 10. In particular, the acid is preferably at least one acid selected from the group consisting of phosphoric acid, lactic acid, benzoic acid, maleic acid, citric acid, tartaric acid, succinic acid, ascorbic acid, and aspartic acid, and more preferably at least one acid selected from the group consisting of phosphoric acid, citric acid, and tartaric acid. The concentration of the acid in the microneedle coating composition 10 is preferably 5% to 50% w/w and more preferably 10% to 30% w/w based on the total mass of the microneedle coating composition 10. In addition, the concentration of the acid in the coating layers 5 prepared by applying the microneedle coating composition 10 to the microneedles 3 and removing the volatile component is preferably 5% to 50% w/w and more preferably 10% to 30% w/w based on the total mass of the coating layers 5.

The microneedle coating composition 10 may comprise, in addition to the Japanese encephalitis vaccine antigen, the basic amino acid, and the acid, an aqueous solution, for example, purified water, physiological saline, or a buffer such as phosphate buffer, citrate buffer, acetate buffer, citrate-phosphate buffer, tris-hydrochloric acid buffer, or glycine-sodium hydroxide buffer. The content of these aqueous solutions is preferably 5% to 75% by mass based on the total mass of the microneedle coating composition 10. A content exceeding 75% by mass tends not to obtain a sufficient viscosity during coating, and a content of less than 5% by mass tends to make the dissolution of the composition difficult.

The microneedle coating composition 10 may comprise, in addition to the above-mentioned basic amino acid, lysine or a pharmaceutically acceptable salt of lysine. The addition of lysine or a pharmaceutically acceptable salt of lysine can further improve the stability of the Japanese encephalitis vaccine antigen.

The pharmaceutically acceptable salt of lysine is preferably hydrochloride. The concentration of lysine hydrochloride may be 0.1% to 20% w/w based on the total mass of the microneedle coating composition 10. In a concentration exceeding 20% w/w, lysine hydrochloride may not be dissolved, and in a concentration of less than 0.1% w/w, the stability of the Japanese encephalitis vaccine antigen may be insufficient. In addition, the concentration of lysine hydrochloride in the coating layer 5 prepared by applying the microneedle coating composition 10 to the microneedles 3 and removing the volatile component may be 0.1% to 20% w/w based on the total mass of the coating layers 5.

In addition, the microneedle coating composition 10 may further comprise a polymer carrier (thickener) as an optional component. Examples of the polymer carrier include polyethylene oxide, polyhydroxymethyl cellulose, hydroxypropyl cellulose, polyhydroxypropyl methylcellulose, polymethyl cellulose, dextran, polyethylene glycol, polyvinyl alcohol, polyvinylpyrrolidone, pullulan, carmellose sodium, chondroitin sulfate, hyaluronic acid, dextran, and gum arabic. The weight-average molecular weight of polyethylene glycol used as the polymer carrier is preferably higher than 600 and not higher than 500000.

The polymer carrier is preferably a carrier having a high compatibility (uniform miscibility) with the Japanese encephalitis vaccine antigen, and particularly preferred examples are hydroxypropyl cellulose, dextran, polyvinyl alcohol, and pullulan.

The content of the polymer carrier in the microneedle coating composition 10 is 0.005% to 30% by mass, preferably 0.01% to 20% by mass, and more preferably 0.05% to 10% by mass, based on the total mass of the microneedle coating composition 10. In addition, this polymer carrier needs to have a certain degree of viscosity for preventing dripping in some cases, and the viscosity at room temperature (25° C.) is preferably 100 to 100000 mPa·s. More preferred viscosity is 500 to 60000 mPa·s.

In addition to the description above, the microneedle coating composition 10 may comprise, as needed, a solubilizing agent or absorption promoter, such as propylene carbonate, crotamiton, L-menthol, peppermint oil, limonene, or diisopropyl adipate, a drug effect auxiliary agent, such as methyl salicylate, glycol salicylate, L-menthol, thymol, peppermint oil, nonylic acid vanillylamide, or capsicum extract.

Furthermore, as needed, the microneedle coating composition 10 may comprise a compound such as a stabilizer, an antioxidant, an emulsifier, a surfactant, or a salt. The surfactant may be a nonionic surfactant or an ionic surfactant (cationic, anionic, or zwitterionic), and is desirably a nonionic surfactant that is usually used as a medicinal base, from a safety standpoint. Examples of these compounds include sugar alcohol fatty acid esters, such as sucrose fatty acid ester, propylene glycol fatty acid ester, polyoxyethylene sorbitan fatty acid ester, polyoxyethylene sorbitan fatty acid ester, polyoxyethylene glycerin fatty acid ester, polyethylene glycol fatty acid ester, polyoxyethylene castor oil, and polyoxyethylene hydrogenated castor oil.

Other known preparation auxiliary materials may be contained in the microneedle coating composition 10, as long as they do not adversely affect the effect of improving the solubility and the viscosity of the microneedle coating composition 10 and do not adversely affect the characteristics and the physical properties of the dried microneedle coating composition 10 adhering to the microneedles 3.

The microneedle coating composition 10 needs to have a certain degree of viscosity for preventing dripping after application onto the microneedles 3. The viscosity is about 100 to 45000 mPa·s, and in the microneedle coating composition 10 having a viscosity within this range, a desired amount of the microneedle coating composition 10 can adhere to the microneedles 3 at a time, without depending on the material of the microneedles.

When the viscosity of the microneedle coating composition 10 at 25° C. is 45000 mPa·s or less, the shear stress is increased to increase the resistance to peeling between materials. Consequently, in application of a drug solution by a dipping method, the property (aggregability) of individuals, i.e., resistance to dissociation from the microneedles, is enhanced, and a larger amount of coating composition can be held on the microneedles. In contrast, if the viscosity exceeds 45000 mPa·s, the content of the Japanese encephalitis vaccine antigen in the coating composition adhering to the microneedles shifts to a decrease, which is economically disadvantageous. When the viscosity of the coating composition is 100 mPa·s or more, since the aggregability is high, it is possible to hold a large amount of coating composition on the microneedles. Based on these characteristics, the viscosity of the microneedle coating composition 10 at 25° C. is preferably 100 to 45000 mPa·s, more preferably 300 to 35000 mPa·s, further preferably 500 to 30000 mPa·s, and particularly preferably 600 to 15000 mPa·s.

EXAMPLES

The present invention will now be more specifically described with reference to Examples of the present invention, but is not limited to these Examples, and can be variously modified within a scope not departing from the technical idea of the present invention.

<Solubility of Mixture of Arginine and Acid in Water>

Arginine was mixed with any of the acids (N valence) shown in Tables 1 to 3 at a ratio, arginine:acid=N:1; purified water was added to each mixture to prepare a dilute solution of 20% w/w arginine-acid; and the water was evaporated by lyophilization to make a lyophilized solid. Purified water was added to this lyophilized solid at a ratio, (the mixture (Arg+acid) of arginine and the acid):water=7:3, to prepare a concentrated solution of the mixture (Arg+acid) of arginine and the acid. In the tables, "solubility" shows the results, wherein the symbol "○" denotes a case in which a concentrated solution could be prepared with complete solubility, and the symbol "Δ" denotes a case in which a part of the lyophilized solid was partially dissolved.

TABLE 1

| Inorganic acid | Hydrochloric acid (monovalent) | Sulfuric acid (divalent) | Methanesulfonic acid (monovalent) | Phosphoric acid (trivalent) |
|---|---|---|---|---|
| Melting point (° C.) | −27.3 | 10 | 20 | 42.4 |
| Solubility | Δ | Δ | Δ | ○ |

TABLE 2

| Organic acid | Glacial acetic acid (monovalent) | Lactic acid (monovalent) | Benzoic acid (monovalent) | Maleic acid (divalent) | Citric acid (trivalent) |
|---|---|---|---|---|---|
| Melting point (° C.) | 16.7 | 53 | 122 | 131 | 153 |
| Solubility | Δ | ○ | ○ | ○ | ○ |

TABLE 3

| Organic acid | Tartaric acid (divalent) | Succinic acid (divalent) | Ascorbic acid (monovalent) | Aspartic acid (monovalent) |
|---|---|---|---|---|
| Melting point (° C.) | 168 | 185 | 190 | 300 |
| Solubility | ○ | ○ | ○ | ○ |

<Solubility in Water and Viscosity Characteristics of Mixture of Arginine and Acid Depending on Blending Ratio>

Arginine and an acid were mixed at the molar ratios shown in Table 4 and 5; purified water was added to each mixture to prepare a dilute solution of 20% w/w arginine-acid; and the water was evaporated by lyophilization to make a lyophilized solid. Purified water was added to this lyophilized solid at a ratio, (the mixture (Arg+acid) of arginine and the acid):water=7:3, to prepare a concentrated solution of the mixture (Arg+acid) of arginine and the acid. In the tables, "solubility" shows the results, wherein the symbol "○" denotes a case in which a concentrated solution could be prepared with complete solubility, the symbol "Δ" denotes a case in which the lyophilized solid was partially dissolved, and the symbol "×" denotes a case in which the lyophilized solid was not substantially dissolved. In the tables, the "viscosity" was measured with a small sample viscometer (VROC, manufactured by RheoSense, Inc.), and the unit thereof is "mPa·s".

In addition, the concentrated solution of each of the mixtures of arginine and an acid (Arg+acid, arginine:phosphoric acid=2:1, arginine:citric acid=3:1, and arginine:tartaric acid=2:1) was applied to a microneedles (height: about 500 μm, density: 640 needles/cm², shape: quadrangular pyramid), and the needle tips of the microneedles were observed with a microscope (VH-8000, manufactured by KEYENCE Corporation). The results of the observation showed that coating layers were formed on the tip portions of the microneedles and demonstrated that the mixtures of arginine and an acid are suitable for application to needle tips.

TABLE 4

| Arg:Phosphoric acid (trivalent) | Solubility | Viscosity | Arg:Citric acid (trivalent) | Solubility | Viscosity |
|---|---|---|---|---|---|
| 1:1 | ○ | — | 1:1 | ○ | — |
| 2:1 | ○ | 1134 | 2:1 | ○ | — |
| 3:1 | ○ | — | 3:1 | ○ | 1331 |
| 4:1 | Δ | — | 4:1 | Δ | — |

TABLE 5

| Arg:Tartaric acid (divalent) | Solubility | Viscosity | Arg:Lactic acid (monovalent) | Solubility | Viscosity |
|---|---|---|---|---|---|
| 1:1 | ○ | — | 1:1 | ○ | — |
| 2:1 | ○ | 792 | 2:1 | Δ | — |
| 3:1 | Δ | — | 3:1 | X | — |
| 4:1 | X | — | 4:1 | X | — |

<Evaluation of Stability of Japanese Encephalitis Vaccine Antigen>

A Japanese encephalitis vaccine antigen application solution blended with arginine and an acid was applied onto microneedles, and stability was evaluated.

A phosphate buffer physiological saline (PBS) solution of a Japanese encephalitis vaccine antigen was used as a bulk drug. This bulk drug was concentrated by ultrafiltration, and Japanese encephalitis vaccine antigen application solutions were prepared by adding a lyophilized solid (Arg+acid) of a mixture of arginine and an acid and lysine hydrochloride (Lys HCl) to the concentrate and mixing them or by mixing arginine, an acid, and lysine hydrochloride with the bulk drug during the concentration and lyophilizing and then redissolving the mixture. The blending ratio (unit: % by mass) of each component and molar ratio of Arg+acid are shown in Table 6.

The resulting Japanese encephalitis vaccine antigen application solutions were each applied to microneedles (height: about 500 μm, density: 640 needles/cm$^2$, shape: quadrangular pyramid) and were dried to obtain formulations A to F. In Table 6, the numerical values in parentheses for each component denote the blending ratios (unit:% by mass) after drying. Formulations A to F were sealed in MoistCatch (trade name, Kyodo Printing Co., Ltd.) together with PharmaKeep (trade name, Mitsubishi Gas Chemical Company, Inc.) and were preserved at 40° C. for one month.

The evaluation of stability was performed by extracting the Japanese encephalitis vaccine antigen from the microneedles with an extraction liquid (0.01% by mass of Tween 80/1% by mass of trehalose/PBS), performing measurement (ELISA) of the content of E antigen and quantitative measurement (Lowry method) of protein, and comparing the E antigen content per protein content as the specific activity after one month at 40° C. with the initial value.

TABLE 6

| Formulation | Japanese encephalitis vaccine antigen | Arg + acid | PBS | Lys•HCl | Acid | Arg + acid Arg:Acid (molar ratio) | Specific activity Initial stage | Specific activity 40° C., 1 month |
|---|---|---|---|---|---|---|---|---|
| A | 0.87 (1.2) | 70 (98.3) | 29.13 (0.5) | 0 (0) | Phosphoric acid (trivalent) | 2:1 | 1.01 | 0.97 |
| B | 3.75 (4.9) | 70 (91.5) | 23.75 (0.4) | 2.5 (3.3) | | | 1.07 | 0.98 |
| C | 3.75 (4.9) | 70 (91.5) | 23.75 (0.4) | 2.5 (3.3) | | 3:1 | 1.23 | 0.96 |
| D | 0.87 (1.2) | 70 (98.3) | 29.13 (0.5) | 0 (0) | Citric acid (trivalent) | 3:1 | 1.02 | 0.87 |
| E | 3.75 (4.9) | 70 (91.5) | 23.75 (0.4) | 2.5 (3.3) | | | 1.00 | 0.98 |
| F | 0.87 (1.2) | 70 (98.3) | 29.13 (0.5) | 0 (0) | Tartaric acid (divalent) | 2:1 | 0.92 | 0.87 |

In formulations A to F, the specific activity of each sample preserved at 40° C. for one month was approximately the same as that of the sample at the initial stage, and no decrease in the activity was observed.

<Blending Effect of Lysine Hydrochloride>

A Japanese encephalitis vaccine antigen application solution comprising 70% by mass of a mixture of arginine and an acid, where the blending ratio of each component (unit: % by mass) and the molar ratio of arginine and the acid are shown in Table 7, was applied onto microneedles, and the blending effect of the lysine hydrochloride was evaluated using an L9 orthogonal table. In Table 7, the numerical values in parentheses for each component denote the blending ratios (unit: % by mass) after removal of the volatile component.

Figure 4:
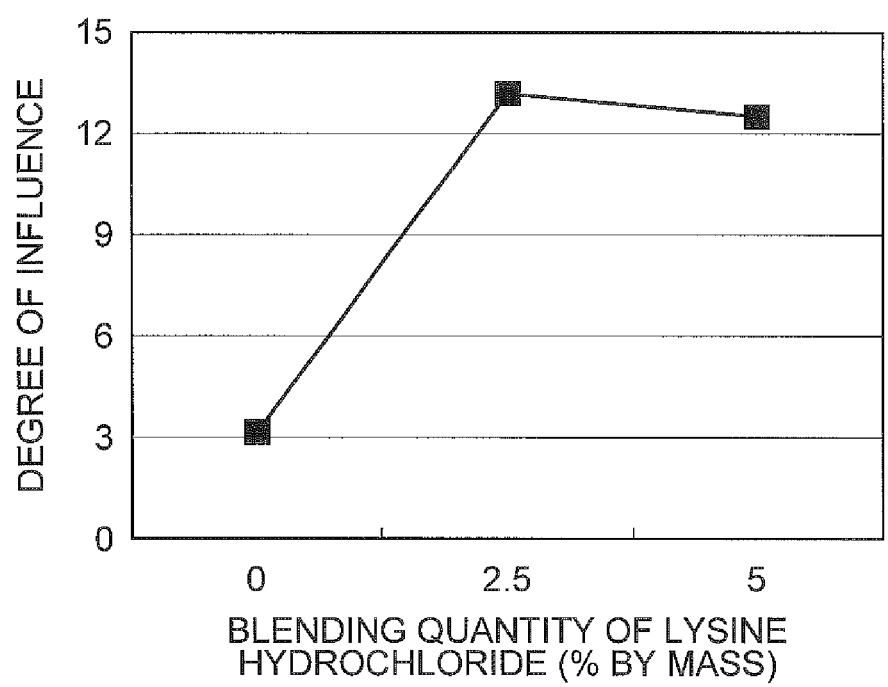
FIG. 4 is a graph showing the degree of influence of lysine hydrochloride on specific activity.

A PBS solution of a Japanese encephalitis vaccine antigen was used as a bulk drug, this bulk drug was concentrated by ultrafiltration, and a predetermined amount of an additive was added to the concentrate, followed by mixing to obtain an application solution for microneedles. This solution was applied to needle tips of polylactic acid microneedles (height: about 500 μm, density: 640 needles/cm², shape: quadrangular pyramid) under an environment of a relative humidity of 80% to 85%. After drying, the microneedles were sealed in MoistCatch (trade name, Kyodo Printing Co., Ltd.) together with PharmaKeep (trade name, Mitsubishi Gas Chemical Company, Inc.), and the stability under each temperature condition was evaluated. After extraction of the Japanese encephalitis vaccine antigen from the microneedles with an extraction liquid (0.01% Tween 80/1% trehalose/PBS), measurement (ELISA) of the content of E antigen and quantitative measurement (Lowry method) of protein were performed, and the E antigen content per protein content was evaluated as the specific activity. For the specific activity level of each sample preserved at 50° C. for 2 weeks, the degree of influence by blending of lysine hydrochloride on the specific activity was analyzed by a least-squares method. FIG. 4 is a graph showing the degree of influence of lysine hydrochloride on the specific activity. When 2.5% or 5.0% of lysine hydrochloride was blended, the degree of influence on the specific activity of the sample preserved at 50° C. for 2 weeks was high, which demonstrates that lysine hydrochloride has an effect of improving the stability.

TABLE 7

| Formulation | Japanese encephalitis vaccine antigen | Arg + acid | Glycine | Lys•HCl | PBS | Arg + acid (molar ratio) | Specific activity 50° C., 2 weeks |
|---|---|---|---|---|---|---|---|
| G | 0.9 (1.3) | 70 (98.3) | 0 (0) | 0 | 29.1 (0.5) | Arg + | 0.84 |
| H | 09 (1.2) | 70 (91.9) | 2.5 (3.3) | 2.5 (3.3) | 24.1 (0.4) | phosphoric acid | 0.82 |
| I | 0.9 (1.1) | 70 (86.3) | 5 (6.2) | 5 (6.2) | 19.1 (0.3) | (2:1) | 0.85 |
| J | 0.9 (1.2) | 70 (95.0) | 0 (0) | 2.5 (3.4) | 26.6 (0.4) | Arg + citric acid | 0.87 |
| K | 0.9 (1.1) | 70 (89.0) | 2.5 (3.2) | 5 | 21.6 (0.3) | (3:1) | 0.92 |
| L | 0.9 (1.2) | 70 (91.9) | 5 (6.6) | 0 | 24.1 (0.4) | | 0.70 |
| M | 0.9 (1.2) | 70 (91.9) | 0 (0) | 5 (6.6) | 24.1 (0.4) | Arg + tartaric | 0.75 |
| N | 0.9 (1.2) | 70 (95.0) | 2.5 (3.4) | 0 | 26.6 (0.4) | acid (2:1) | 0.70 |
| O | 0.9 (1.1) | 70 (89.0) | 5 (6.4) | 2.5 (3.2) | 21.6 (0.3) | | 0.85 |

<Stability Evaluation of Japanese Encephalitis Vaccine Antigen by Preparation Dosage>

The Japanese encephalitis vaccine antigen application solution blended with arginine and an acid was applied onto microneedles, and the stabilities in two different dosages of a preparation, 4 μg of the preparation and 0.2 μg of the preparation, were evaluated. The two different dosages of the preparation were made by adjusting the antigen concentration of the Japanese encephalitis vaccine antigen application solution and application height.

A phosphate buffer physiological saline (PBS) solution of a Japanese encephalitis vaccine antigen was used as a bulk drug. This bulk drug was concentrated by ultrafiltration, and Japanese encephalitis vaccine antigen application solutions were prepared by mixing the bulk drug with arginine, phosphoric acid, and lysine hydrochloride during the concentration and lyophilizing and then redissolving the mixture. The blending ratio (unit: % by mass) of each component and molar ratio of Arg+acid are shown in Table 8.

The resulting Japanese encephalitis vaccine antigen application solutions were applied to microneedles (height: about 500 μm, density: 640 needles/$cm^2$, shape: quadrangular pyramid) to obtain formulation P of an application height of 125 μm and an expected content of 4 μg, formulation Q an application height of 70 μm and an expected content of 0.2 μg, formulation R of an application height of 120 μm and an expected content of 8 μg, formulation S of an application height of 60 μm and an expected content of 2 μg, formulation T of an application height of 60 μm and an expected content of 1 μg, and formulation U of an application height of 60 μm and an expected content of 0.032 μg. In Table 8, the numerical values in parentheses for each component denote the blending ratios (unit:% by mass) after drying. Formulations P to U were sealed in MoistCatch (trade name, Kyodo Printing Co., Ltd.) together with PharmaKeep (trade name, Mitsubishi Gas Chemical Company, Inc.), and formulations P to T were preserved for three months and formulation U was preserved for four months, under each temperature condition shown in Table 9.

The evaluation of stability was performed by extracting the Japanese encephalitis vaccine antigen from the microneedles with an extraction liquid (0.01% by mass of Tween 80/1% by mass of trehalose/PBS), performing measurement (ELISA) of the content of E antigen and quantitative measurement (Lowry method) of protein, and comparing the E antigen content per protein content as the specific activity. In formulations Q and U of low dosages, the specific activity was determined by calculation from the measured value of amino acid content and the blending ratio in the formulation instead of the protein content measured by the Lowry method. The amino acid content was measured by the ortho-phthalaldehyde (OPA) method.

TABLE 8

| Formulation | Japanese encephalitis vaccine antigen application solution: Japanese encephalitis vaccine antigen | Arg + acid | PBS | Lys•HCl | Arg + acid: Acid | Arg + acid: Arg:acid (molar ratio) | Application height (μm) | Expected content (μg) |
|---|---|---|---|---|---|---|---|---|
| P | 3.75 (4.9) | 70 (91.5) | 23.75 (0.4) | 2.5 (3.3) | Phosphoric acid (trivalent) | 2:1 | 125 | 4 |
| Q | 0.75 (1.0) | 70 (95.2) | 26.75 (0.4) | 2.5 (3.4) | | | 70 | 0.2 |
| R | 6.5 (9.3) | 60.7 (87.0) | 30.7 (0.5) | 2.2 (3.2) | | | 120 | 8 |
| S | 6.5 (9.3) | 60.7 (87.0) | 30.7 (0.5) | 2.2 (3.2) | | | 60 | 2 |
| T | 3.75 (4.9) | 70 (91.5) | 23.75 (0.4) | 2.5 (3.3) | | | 60 | 1 |
| U | 0.11 (0.15) | 70 (96.0) | 27.4 (0.4) | 2.5 (3.4) | | | 60 | 0.032 |

TABLE 9

| Formulation | Item | Initial stage | 10° C., 3 months | 25° C., 3 months | 40° C., 3 months | 50° C., 3 months |
|---|---|---|---|---|---|---|
| P | Protein content | 4.22 | 4.70 | 4.60 | 4.37 | 4.44 |
| | | 100.0% | 111.5% | 109.2% | 103.8% | 105.3% |
| | E antigen content | 5.82 | 6.08 | 5.98 | 5.83 | 5.22 |
| | | 100.0% | 104.6% | 102.8% | 100.2% | 89.8% |
| | Specific activity | 1.38 | 1.29 | 1.30 | 1.33 | 1.18 |
| Q | Protein content | 0.208 | 0.204 | 0.213 | 0.210 | 0.210 |
| | | 100.0% | 98.1% | 102.2% | 101.0% | 100.8% |
| | E antigen content | 0.239 | 0.246 | 0.231 | 0.228 | 0.213 |
| | | 100.0% | 103.1% | 96.9% | 95.6% | 89.3% |
| | Specific activity | 1.15 | 1.20 | 1.09 | 1.08 | 1.01 |
| R | Protein content | 7.06 | | 7.50 | 7.37 | 7.37 |
| | | 100.0% | | 106.2% | 1.04.3% | 104.3% |
| | E antigen content | 7.86 | | 8.15 | 8.03 | 8.58 |
| | | 100.0% | | 103.7% | 102.1% | 109.2% |
| | Specific activity | 1.11 | | 1.09 | 1.09 | 1.16 |
| S | Protein content | 1.84 | | 1.98 | 1.81 | 1.88 |
| | | 100.0% | | 107.7% | 98.3% | 102.1% |
| | E antigen content | 1.73 | | 1.86 | 1.66 | 1.49 |
| | | 100.0% | | 107.6% | 95.8% | 86.1% |
| | Specific activity | 0.94 | | 0.94 | 0.92 | 0.79 |
| T | Protein content | 1.17 | | 1.22 | 1.22 | 1.14 |
| | | 100.0% | | 104.4% | 104.9% | 97.7% |

TABLE 9-continued

| Formulation | Item | | Initial stage | 10° C., 4 months | 25° C., 4 months | 40° C., 4 months | 50° C., 4 months |
|---|---|---|---|---|---|---|---|
| | E antigen content | | 1.38 100.0% | | 1.24 89.6% | 1.25 90.4% | 1.22 88.7% |
| | Specific activity | | 1.18 | | 1.01 | 1.02 | 1.07 |
| U | Protein content | | 0.033 100.0% | 0.033 97.4% | 0.033 97.5% | 0.035 104.1% | 0.031 94.0% |
| | E antigen content | | 0.032 100.0% | 0.032 100.0% | 0.026 81.3% | 0.032 100.0% | 0.028 87.5% |
| | Specific activity | | 0.96 | 0.98 | 0.80 | 0.92 | 0.89 |

In formulations P to T, no decreases in protein content and E antigen content were observed in the samples preserved at a temperature of 10° C., 25° C., 40° C., or 50° C. for three months, compared to those of the samples at the initial stage. Also in formulation U, no decreases in protein content and E antigen content were observed in the samples preserved at a temperature of 10° C., 25° C., 40° C., or 50° C. for four months, compared to those of the samples at the initial stage. The specific activity was also approximately the same level, and thus no decrease in activity was observed.

REFERENCE SIGNS LIST

1: microneedle device, 2: substrate, 3: microneedle, 5: coating layer, 10: microneedle coating composition, 11: mask plate, 12: spatula, 13: opening portion

The invention claimed is:

1. A microneedle coating composition comprising:
a Japanese encephalitis vaccine antigen;
a basic amino acid in a concentration of 20% w/w or more based on the total mass of the microneedle coating composition; and
an acid in a concentration of 5% to 50% w/w based on the total mass of the microneedle coating composition, wherein the acid is at least one acid selected from the group consisting of phosphoric acid, lactic acid, benzoic acid, maleic acid, citric acid, tartaric acid, succinic acid, ascorbic acid and aspartic acid, wherein
a mole number of the acid for one mole of the basic amino acid is larger than 1/(N+1) and less than 2, where N represents a valence of the acid.

2. The microneedle coating composition according to claim 1, wherein the acid has a melting point of 40° C. or more.

3. The microneedle coating composition according to claim 1, wherein the basic amino acid is arginine.

4. The microneedle coating composition according to claim 3, comprising lysine or lysine hydrochloride.

5. The microneedle coating composition according to claim 1, comprising lysine or lysine hydrochloride.

6. The microneedle coating composition according to claim 1, wherein a concentration of the basic amino acid is 30% w/w or more based on the total mass of the microneedle coating composition.

7. A microneedle device comprising:
a microneedle; and
a coating layer formed from the microneedle coating composition according to claim 1 on the microneedle.

8. The microneedle device according to claim 7, wherein the coating layer is formed on a tip portion of the microneedle.

9. A microneedle device comprising:
a microneedle; and
a coating layer formed from the microneedle coating composition according to claim 3 on the microneedle.

10. A microneedle device comprising:
a microneedle; and
a coating layer formed from the microneedle coating composition according to claim 4 on the microneedle.

* * * * *

UNITED STATES PATENT AND TRADEMARK OFFICE
CERTIFICATE OF CORRECTION

PATENT NO. : 9,849,170 B2
APPLICATION NO. : 14/766922
DATED : December 26, 2017
INVENTOR(S) : Kazuya Machida et al.

Page 1 of 1

It is certified that error appears in the above-identified patent and that said Letters Patent is hereby corrected as shown below:

Please delete:
"(71) Applicant: THE CHEMO-SERO-THERAPEUTIC RESEARCH INSTITUTE, Kumamoto-shi, Kumamoto, JP"
And replace with following:
(71) Applicant: HISAMITSU PHARMACEUTICAL CO., INC. Tosu-Shi, Saga, JP

AND

Please delete:
"(73) Assignee: THE CHEMO-SERO-THERAPEUTIC RESEARCH INSTITUTE, Kumamoto-shi, Kumamoto, JP"
And replace with following:
(73) Assignee: HISAMITSU PHARMACEUTICAL CO., INC. Tosu-Shi, Saga, JP Signed and Sealed this
Twenty-seventh Day of November, 2018

Andrei Iancu
*Director of the United States Patent and Trademark Office*